United States Patent
Bernhart et al.

(10) Patent No.: US 10,792,063 B2
(45) Date of Patent: Oct. 6, 2020

(54) DEVICE FOR RETAINING AND MOVING A LAPAROSCOPE DURING AN OPERATION

(71) Applicant: MAQUET GMBH, Rastatt (DE)

(72) Inventors: Michael Bernhart, Karlsruhe (DE); Lena Ginzinger, Baden-Baden (DE); Mike Obert, Gernsbach (DE)

(73) Assignee: MAQUET GMBH, Rastatt (DE)

( * ) Notice: Subject to any disclaimer, the term of this patent is extended or adjusted under 35 U.S.C. 154(b) by 539 days.

(21) Appl. No.: 15/654,118

(22) Filed: Jul. 19, 2017

(65) Prior Publication Data

US 2017/0311969 A1 Nov. 2, 2017

Related U.S. Application Data

(63) Continuation of application No. PCT/EP2016/051190, filed on Jan. 21, 2016.

(30) Foreign Application Priority Data

Jan. 23, 2015 (DE) .................. 10 2015 101 018

(51) Int. Cl.
*A61B 34/30* (2016.01)
*A61B 17/32* (2006.01)
(Continued)

(52) U.S. Cl.
CPC .... *A61B 17/32002* (2013.01); *A61B 17/7085* (2013.01); *A61B 34/30* (2016.02);
(Continued)

(58) Field of Classification Search
USPC .......................................... 606/1
See application file for complete search history.

(56) References Cited

U.S. PATENT DOCUMENTS

| 4,551,058 A | 11/1985 | Mosher |
| 5,078,140 A | 1/1992 | Kwoh |

(Continued)

FOREIGN PATENT DOCUMENTS

| DE | 19609034 A1 | 9/1996 |
| DE | 10305693 B4 | 2/2006 |

(Continued)

OTHER PUBLICATIONS

Translated International Search Report (completed Apr. 22, 2016—dated May 4, 2016) which issued for corresponding international application PCT/EP2016/051190, 3 pages.

*Primary Examiner* — Michael W Kahelin
*Assistant Examiner* — Shirley X Jian (57) ABSTRACT

The invention relates to a device for retaining and moving a laparoscope during an operation, which comprises a securing unit for securing on a retaining arm, a receiving unit for retaining the laparoscope, as well as a main body. Furthermore, the device has a lever via which the receiving unit is secured to the main body. The main body is mounted on the securing unit in a rotatable manner about a first rotation axis via a first rotation unit. The lever is mounted on the main body in a rotatable manner about a second rotation axis via a second rotation unit. Furthermore, a first drive unit is provided, which, upon activation, drives the first and the second rotation unit in such a manner that the main body is rotated about the first rotation axis, and the lever is rotated about the second rotation axis by the same rotation angle in the opposite rotation direction.

20 Claims, 10 Drawing Sheets

(51) Int. Cl.
   *A61B 90/50* (2016.01)
   *A61B 34/00* (2016.01)
   *A61B 17/70* (2006.01)
   A61B 17/00 (2006.01)
   A61M 25/00 (2006.01)

(52) U.S. Cl.
   CPC .............. *A61B 34/70* (2016.02); *A61B 90/50* (2016.02); *A61B 2017/00017* (2013.01); *A61B 2017/00389* (2013.01); *A61B 2034/302* (2016.02); *A61M 2025/0006* (2013.01)

(56) References Cited

U.S. PATENT DOCUMENTS

| | | | |
|---|---|---|---|
| 5,766,126 A | 6/1998 | Anderson | |
| 5,976,156 A | 11/1999 | Taylor et al. | |
| 6,024,695 A | 2/2000 | Taylor et al. | |
| 6,932,089 B1 | 8/2005 | Cinquin et al. | |
| 8,167,872 B2 * | 5/2012 | Schena | A61B 34/70 606/1 |
| 2003/0167061 A1 | 9/2003 | Schlegel et al. | |
| 2003/0221504 A1 | 12/2003 | Stoianovici et al. | |
| 2005/0234293 A1 | 10/2005 | Yamamoto et al. | |
| 2006/0100501 A1 | 5/2006 | Berkelman et al. | |
| 2007/0089557 A1 | 4/2007 | Solomon et al. | |
| 2009/0112056 A1 | 4/2009 | Finlay | |
| 2010/0168765 A1 | 7/2010 | Moraviec | |
| 2011/0028992 A1 | 2/2011 | Geiger et al. | |
| 2011/0257475 A1 | 10/2011 | Berkelman et al. | |
| 2012/0041263 A1 | 2/2012 | Sholev | |
| 2014/0276953 A1 | 9/2014 | Swarup et al. | |

FOREIGN PATENT DOCUMENTS

| | | |
|---|---|---|
| DE | 102006007858 A1 | 8/2007 |
| DE | 102007019363 B4 | 6/2009 |
| DE | 102008016146 B4 | 1/2010 |
| DE | 102009018917 A1 | 11/2010 |
| DE | 102013002818.3 A1 | 8/2014 |
| DE | 102013012802.1 A1 | 2/2015 |
| EP | 0761177 B1 | 4/2002 |
| EP | 2008605 A1 | 12/2008 |
| EP | 2052675 A1 | 4/2009 |
| EP | 2246006 A2 | 11/2010 |
| EP | 2254735 B1 | 7/2011 |
| EP | 2457533 A2 | 5/2012 |
| EP | 2520244 A1 | 11/2012 |
| EP | 2169346 B1 | 9/2014 |

\* cited by examiner

DEVICE FOR RETAINING AND MOVING A LAPAROSCOPE DURING AN OPERATION

CROSS REFERENCE TO RELATED APPLICATIONS

The present application is a continuation-in-part filed under 35 U.S.C. § 111(a), and claims the benefit under 35 U.S.C. §§ 365(c) and 371 of PCT International Application No. PCT/EP2016/051190, filed Jan. 21, 2016, which designates the United States of America, and claims benefit of German Patent Application No. 10 2015 101 018.6, filed Jan. 23, 2015. The disclosure of each of these applications is incorporated by reference herein in its entirety.

TECHNICAL FIELD

The invention relates to a device for retaining and moving a laparoscope during an operation, which comprises a securing unit for securing the device on a retaining arm as well as a receiving unit for retaining the laparoscope.

BACKGROUND

During laparoscopic interventions, the surgeon looks at the surgical site indirectly via a monitor, on which the laparoscopic instruments with which he/she manipulates the anatomic structures and organs of the patients can be seen. The image which is displayed in real time on the monitor is recorded with a camera which is secured to an optical system which is also introduced laparoscopically and which is oriented toward the surgical site.

The laparoscope with the camera here always needs to be directed onto the area in which the surgeon is currently working. If the field of view to be observed has to be changed, then the laparoscope with the camera needs to be moved so that the desired area is again in the center of the image represented.

All the movements of the laparoscope needed for the repositioning can be composed of three movements. The first movement, the so-called PAN movement, represents a swiveling of the laparoscope about the trocar point, i.e., in that a rotation about a z axis perpendicular to the patient support surface occurs. The second movement required is the so-called TILT movement, during which a tilting of the laparoscope about the trocar point occurs. Thus, during the TILT movement, a rotation about a rotation axis in the xy plane occurs, that is to say in a plane parallel to the patient support surface. The third movement required is the ZOOM movement, in which an enlargement or reduction of the visible field of view occurs due to shifting of the laparoscope along the longitudinal axis thereof. During this ZOOM movement, the laparoscope is thus moved translationally along an axis through the trocar point.

The three movement directions described above are illustrated in FIG. 1. The laparoscope is here marked with the reference numeral 100 and the trocar point is marked with the reference numeral 102.

In order to achieve a continuous repositioning, that is to say a "smooth" movement of the field of view, a combination of a PAN movement and a TILT movement is necessary as a rule.

In most cases the repositioning of the laparoscope is carried out manually by an intern.

As an alternative to manual repositioning, retaining devices for laparoscopes which are capable of performing the repositioning of the laparoscope are also known.

Most such retaining systems have a very complex structure, so that even the performance of a simple TILT or ZOOM requires the activation of several motors for the activation of different articulations. For example, an expensive activation is thus necessary and it may be necessary to use interpolations for the activation.

Devices for retaining and moving a laparoscope are known, for example, from the documents EP 0 761 177 B1, U.S. Pat. No. 5,766,126 A, EP 2 169 346 B1, EP 2 520 244 A1, US 2010/168765 A1, EP 2 052 675 A1, US 2009/0112056 A1, U.S. Pat. No. 6,932,089 B1, US 2006/0100501 A1, US 2011/0257475 A1, DE 103 05 693 B4, DE 10 2006 007 858 A1, DE 10 2007 019 363 B4, DE 10 2008 016 146 B4, EP 2 254 735 B1, US 2011/028992 A1, DE 10 2009 018 917 A1, EP 2 246 006 A2, EP 2 457 533 A2, U.S. Pat. Nos. 5,976,156, 6,024,695 A, DE 196 09 034 C2 and EP 2 008 605 A1.

SUMMARY OF THE DISCLOSURE

It is the aim of the invention to indicate a device for retaining and moving a laparoscope during an operation, which has a simple and compact structure and which can be controlled easily.

This aim is achieved by a device having the features of claim 1. Advantageous developments of the invention are indicated in the dependent claims.

According to the invention, the device comprises a securing unit for securing the device on a retaining arm, which itself in turn is secured on an operating table. Furthermore, the device has a receiving unit for retaining the laparoscope, a main body, and a lever via which the receiving unit is secured to the main body. Here, the main body is mounted with the aid of a first rotation unit on the securing unit in such a manner that the main body is rotatable about a first rotation axis relative to the securing unit. The lever itself is secured with the aid of a second rotation unit on the main body in such a manner that the lever is rotatable about a second rotation axis which is parallel to the first rotation axis relative to the main body. Furthermore, the device comprises a first drive unit for driving the first and the second rotation unit, which, upon activation, drives the first and second rotation units in such a manner that the main body is rotated about the first rotation axis and the lever is rotated about the second rotation axis, wherein the rotation of the main body about the first rotation axis and the rotation of the lever about the second rotation axis occur in the opposite rotation direction but with the same rotation angle.

Thereby, it is achieved that the suspension point of the laparoscope is moved on a circular path about the trocar point, so that it is possible, in a simple manner, via only the two rotation units, to perform the tilting movement, that is to say the TILT movement, of the laparoscope. The orientation of the laparoscope is established in the process by the bearing point which is moved on the circular path and by the trocar point itself. The above-described device thus makes possible a direct driving of the TILT movement, i.e., in that this TILT movement does not have to be composed of several movements, but can occur instead exclusively by means of the first drive unit.

Before the operation, the device is oriented in such a manner that the pivot point of the TILT movement corresponds to the trocar point.

Thus, a simple electronic activation is achieved. No axis interpolation is necessary.

The first rotation unit comprises a first shaft on which the securing unit is mounted in a rotationally fixed manner.

Accordingly, the second rotation unit as well comprises a second shaft on which the lever is mounted in a rotationally fixed manner. Via the first drive unit, the first and the second shaft are always rotated by the same rotation angle but in opposite rotation directions. As a result of this synchronous opposite rotation about two parallel axes, the guidance of the securing point of the laparoscope, which has already been described above, on a circular path about the trocar point, which enables the TILT movement, occurs in a simple manner.

In an exemplary embodiment of the invention, the first drive unit comprises exactly one motor via which both the first as well as the second rotation unit are driven in accordance with the manner described above. For this purpose, an upright shaft is provided, which is driven by the single motor and which is in engagement with both rotation units in such a manner that they are rotated in opposite directions by the same rotation angle. The above-described drive unit has the advantage that, due to the fact that only one motor is provided, only a small installation space is necessary, and thus the main body can be designed very small, which leaves much room for the surgeon. In addition, the exclusively mechanical coupling of the single motor via the upright shaft to the two rotation units offers the assurance that a synchronous rotation always occurs without the need of expensive sensors and electrical activations for this purpose.

The upright shaft is a telescopic upright shaft, such that, as will be described in further detail below, in the design of a zoom function via two housing parts which can be moved linearly toward one another, in spite of the change in distance between the two rotation units, the two rotation units can be reliably driven via the single motor.

It is advantageous if, on the two end areas of the upright shaft, in each case a worm gear or bevel gear wheel arrangement is provided, by means of which the upright shaft is in engagement with the first and the second rotation unit, respectively. On the end areas of the upright shaft, a worm is provided in each case, which is in engagement in each case with a worm gear arranged on the first and the second shaft, respectively, of the rotation units. In this way, it is possible to ensure a reliable force transfer in a simple manner and with compact structure. Furthermore, self-locking is also achieved thereby.

In an alternative embodiment of the invention, it is also possible to use, instead of an upright shaft, a belt drive or a chain drive, wherein the latter too comprises compensation elements for enabling the translational ZOOM movement. In the case of such belt or chain drives, a reduction stage is also inserted, which converts the different rotational of the two rotation units.

Moreover, alternatively, a hydraulic coupling of the motor to the two rotation units is also possible.

In an alternative embodiment of the invention, the first drive unit can also comprise two motors, for example two step motors, wherein one of these two motors is used for driving the first rotation unit, and the other motor is used for driving the second rotation unit. Furthermore, for example, a control unit is provided, which activates the two motors in such a manner that they rotate the rotation units synchronously in opposite directions. For example, sensors are provided, which detect the rotational movement of the two rotation units, and these signals are accordingly taken into consideration in the activation of the two motors. In this way, step losses that may occur in the case of step motors can be compensated.

For example, the receiving unit is designed in such a manner that the laparoscope is mounted by means of it in such a manner that it can rotate freely on the lever. The laparoscope is capable, for example, of rotating freely about an axis which extends parallel to the first and the second rotation axis. Thus, a point guidance of the laparoscope is achieved. In the case of such a point guidance, only the suspension point of the laparoscope is moved, as described above, via the corresponding TILT drive. The orientation of the laparoscope during the operation thus is achieved just in the interaction with a trocar point through which the laparoscope is passed. Such a point guidance has the advantage that it can have a simple mechanical structure. In addition, it has the advantage that, if deviations occur between the virtual pivot point, that is to say the pivot point about which the laparoscope is rotated by the device, and the trocar point, in contrast to vector guidance, only small forces are exerted due to the movement of the laparoscope via the laparoscope onto the abdominal wall of the patient, so that injuries to the patient and/or damage to the laparoscope are avoided.

In an alternative embodiment of the invention, the laparoscope can also be forcibly guided via vector guidance. In this case, for example, in the lever, a parallel crank is integrated, via which the rotation of the laparoscope relative to the lever is controlled. Thus, vector guidance is achieved in a simple manner.

In an exemplary embodiment of the invention, the main body of the device comprises a housing which comprises a first housing part and a second housing part separate from the first housing part. For example, the two housing parts are not secured directly to one another, and they are manufactured from a hard material that is only slightly deformable, for example, metal or plastic. The first rotation unit is secured for example on the first housing part and the second rotation unit on the second housing part.

Furthermore, it is advantageous if a second drive unit is provided, with the aid of which the second housing part can be linearly moved relative to the first housing part in a predetermined direction along a predetermined distance. Via the movement of the two housing parts relative to one another, the distance between the two rotation units, and thus the distance between the securing units mounted on said rotation units and the lever is varied. Thereby, the laparoscope secured to the lever is thus also moved linearly along the longitudinal axis thereof without any change in the tilting, and thus it is moved deeper into the patient or out of the patient. Thus, a ZOOM movement can be performed in a simple manner, and the represented image section can be enlarged or reduced.

As in the case of the TILT movement, a direct driving is also provided, so that the ZOOM movement as well does not need to be composed of several separate movements, but rather is ensured exclusively by an adjustment of the distance between the two housing parts by means of the second drive unit.

The second drive unit comprises for example a motor which drives a spindle via which the two housing parts are coupled to one another. By rotating the spindle, depending on the rotation direction, the second housing part is moved toward the first housing part or away from it.

Furthermore, it is advantageous if the first and the second housing part are connected to one another via at least one linear guide, via several linear guides. Via the linear guides, it is achieved that the two housing parts are reliably secured to one another, and thus greater forces can also be transferred without the occurrence of deformation, tensioning and/or damage, so that the desired orientation of the laparoscope is always maintained.

The linear guides are designed for example in the form of rails that can be shifted together or in the form of round guides mounted in the ball bushings.

Furthermore, the housing comprises a foldable bellows which is arranged between the first and the housing part. In this manner, it is achieved that, even when the distance between the two housing parts is changed for the ZOOM movement, a closed housing is provided at all times, so that damage to the internal parts and also injuries to persons due to jamming between the two housing parts are prevented. Alternatively, instead of a foldable bellows, a telescopic sheet metal cover can also be used.

Alternatively, the first housing part can also be capable of being shifted at least partially onto the second housing part, or the second housing part is capable of being shifted at least partially onto the first housing part. As a result, it is achieved that the housing does not require an intermediate element the length of which can be changed between the two housing parts, since, in spite of the longitudinal displacements necessary for the ZOOM movements, using only the two housing parts, a closed housing is always provided, so that, on the one hand, damage to the internal parts and, on the other hand, injuries to persons due to jamming between the two housing parts are prevented. Furthermore, force transmission directly between the two housing parts is made possible thereby, so that, for example, the linear guides can be dispensed with.

Furthermore, it is advantageous if the first drive unit and the second drive unit, the first rotation unit, the second rotation unit, the linear guides and/or the spindle are arranged within the housing of the main body. Thus, on the one hand, a very compact construction is achieved, and, on the other hand, a protection of these components is ensured. For example, the first and the second rotation axis of the rotation units exclusively project from the housing on which the securing units and the lever are then arranged.

Furthermore, it is advantageous if the securing unit comprises a first section and a second section, wherein the first section is arranged between the second section and the main body and is rotatable about a third rotation axis relative to the second section. Via the rotation of the first section relative to the second section and thus the rotation of the main body relative to the retaining arm, a corresponding rotation of the laparoscope about the third rotation axis occurs. The device is oriented before the operation in such a manner that this third rotation axis extends through the trocar point and, for example, is arranged orthogonally with respect to the plane of the patient support surface. Thus, by the rotation about the third rotation axis, the PAN movement is performed.

The PAN movement is thus also designed as direct drive, i.e., in that for this purpose as well only the activation of one drive unit is necessary in order to perform the rotational movement about the third rotation axis. Due to the combination of the PAN and TILT movements, the point at which the laparoscope is mounted in a rotatable manner on the lever, overall can be moved on a spherical surface with the trocar point as center of the sphere, so that the laparoscope is accordingly swiveled and tilted due to the guidance in the trocar point.

For example, a third drive unit for the rotation of the first section relative to the second section is provided, wherein the third drive unit also comprises, for example, a motor. This motor is arranged, for example, within the housing of the securing unit, within the housing of the first section.

Alternatively, the motor of the third drive unit can also be arranged within the housing of the main body and perform the rotational movement via corresponding coupling arrangements. Due to the arrangement of the third drive unit in the securing unit and/or the main body, it is achieved that the PAN movement is also performed exclusively by parts which are part of the device. Thus, the retaining arm on which the device is secured can be designed to be very simple and purely passive. For example, this retaining arm also does not need to comprise electrical components which perform the PAN movement.

In an alternative embodiment of the invention, the third drive unit can be arranged in the retaining arm, which then has the advantage that the third drive unit does not need to be rotated together with the main body. Furthermore, in this case, as securing unit, the connection between the retaining arm and the main body can be designed to be relatively slender, for example, in the form of a slender fork or a one-sided rocker.

The third axis about which the PAN movement is carried out, is arranged, for example, orthogonally to the first and second rotation axes.

The control of the movement of the laparoscope with the aid of the device occurs, for example, with the aid of image processing programs.

In addition, on the main body, for example, a small joystick can be provided, by means of which, for example, in the case of a failure of the image control process, a control of the movement of the device of the laparoscope can also occur.

BRIEF DESCRIPTION OF THE DRAWINGS

Additional features and advantages of the invention result, for example, from the following description which explains the invention in further detail in reference to embodiment examples in connection with the accompanying figures.

DETAILED DESCRIPTION AND INDUSTRIAL APPLICABILITY

Figure 1:
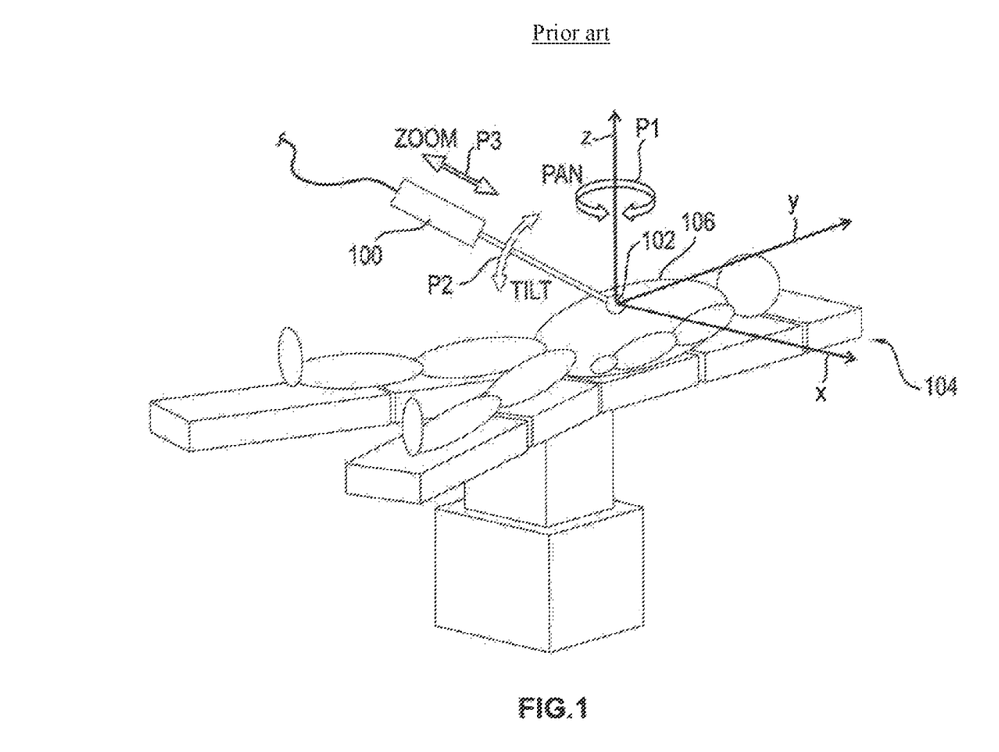
FIG. 1 shows a diagrammatic representation of the three basic movements of a laparoscope during an operation.

In FIG. 1, a diagrammatic representation of a patient 106 lying on a patient support surface 104 during a laparoscopic operation is represented. The laparoscope 100 is introduced by means of a trocar point 102 into the abdominal cavity of the patient 106. Here, with the aid of a camera of a laparoscope 100, images of the operating area are recorded. Here the laparoscope always needs to be repositioned subsequently to track the current operating area, for example in such a manner that the currently manipulated area in the abdominal cavity of the patient 106 is arranged in the middle of the image shown on the monitor which is not represented.

The repositioning movement can be reduced to three basic movements. On the one hand, the laparoscope 100 can be rotated about a z axis which is perpendicular to the patient support surface 104, which is referred to as PAN movement. This thus involves a pivoting of the laparoscope 100 in the direction of the double arrow P1 about the trocar point 102.

Furthermore, the laparoscope 100, as represented by the arrow P2, can be tilted relative to the trocar point 102, which represents a rotation about an axis located in the xy-plane. This tilting of the laparoscope 100 is referred to as TILT movement.

The third basic movement is the ZOOM movement, in which the laparoscope 100 is moved into or out of the patient 106 in accordance with the double arrow P3, so that an enlargement or reduction of the visible image section occurs. Thus, in the ZOOM movement, a translational movement of the laparoscope 100 along its own longitudinal axis occurs.

Figure 2:
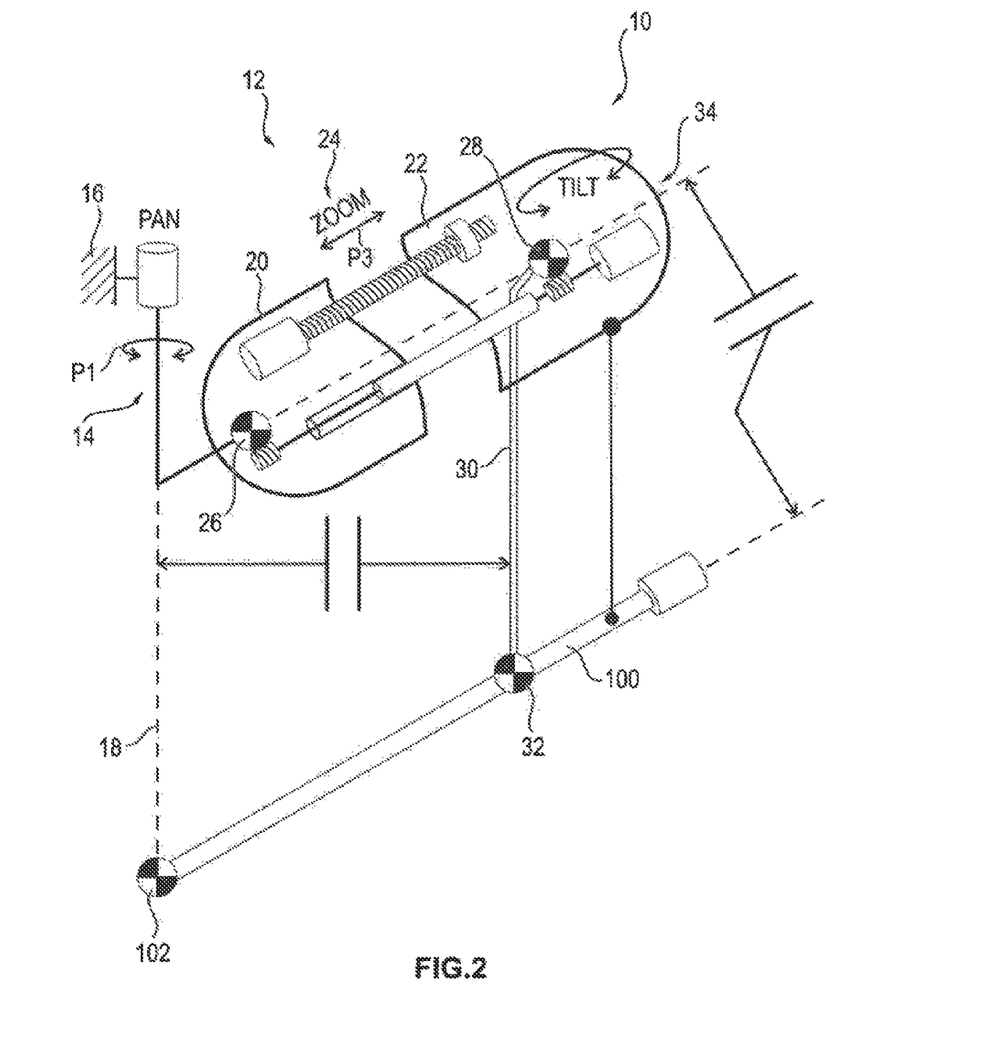
FIG. 2 shows a diagrammatic representation of the general function of a device according to the invention for retaining and moving a laparoscope.

In FIG. 2, a purely diagrammatic representation of the functioning of a device according to the invention for retaining and moving a laparoscope 100 during an operation is shown.

Figure 7:
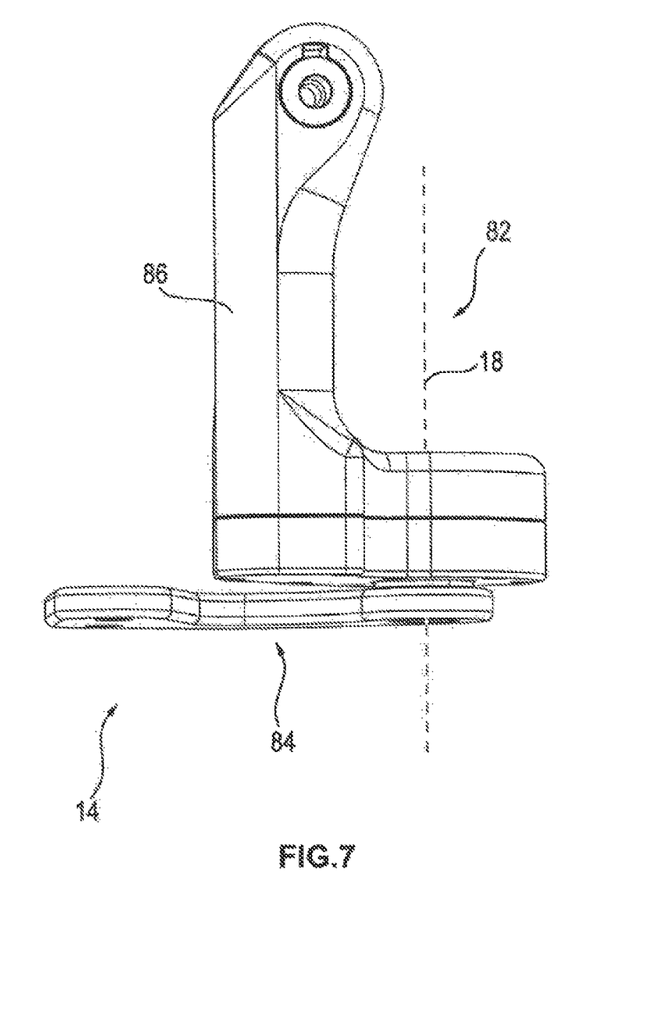
FIG. 7 shows a diagrammatic perspective representation of the securing element according to FIGS. 1 to 6.
Figure 8:
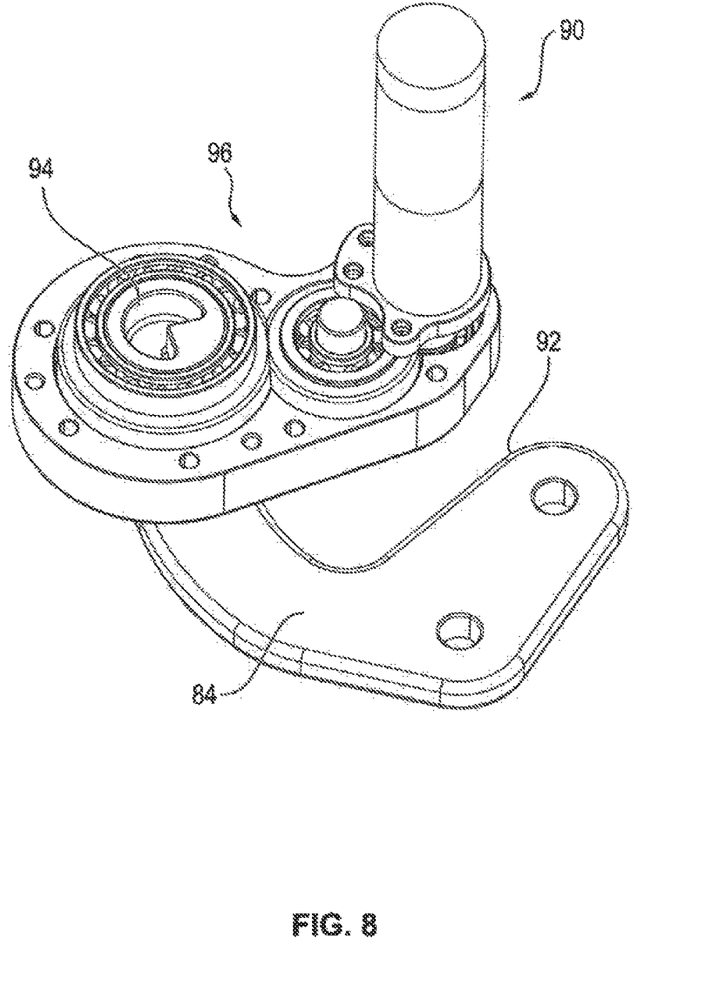
FIG. 8 shows a diagrammatic perspective representation of the securing unit according to FIG. 7 with the housing not shown.
Figure 9:
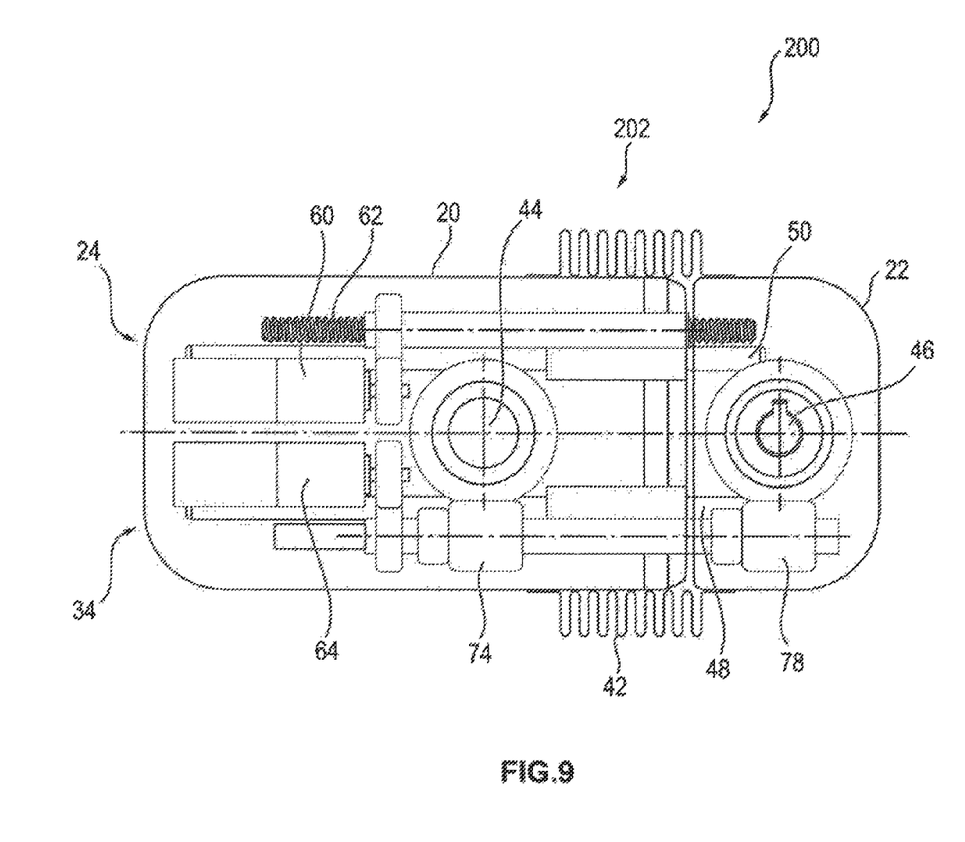
FIG. 9 shows a diagrammatic representation of a main body of a device for retaining and moving a laparoscope according to a second embodiment.

FIGS. 3 to 8 show a concrete first embodiment; FIG. 9 shows a second embodiment and FIG. 10 a third embodiment.

The device 10 comprises a main body 12 which can be secured via a securing unit 14 to a retaining arm 16. For example, this retaining arm 16 is a kind of: stand which can be secured on lateral slide rails of the operating table.

The securing unit 14 is here designed in such a manner that via it the PAN movement is carried out, in that the main body 12 is moved via the securing unit 14 relative to the retaining arm 16 about a third rotation axis 18, which extends through the trocar point 102 and is oriented perpendicularly with respect to the patient 106.

The main body 12 has two housing parts 20, 22 which can be moved linearly with the aid of a second drive unit 24 relative to one another in direction of the double arrow P3. Via the setting of the distance between the two housing parts 20, 22 the ZOOM movement is carried out.

The main body 12 is mounted on the securing unit 14 in such a manner that it can be rotated relative to the securing unit 14 about a first rotation axis with the aid of a first rotation unit 28. This first rotation unit 26 is arranged here on the first housing part 20 of the main body 12.

On the second housing part 22, a second rotation unit 26 is provided, on which a lever 30 is secured. The second rotation unit 28 is used for the rotation of the lever 30 about a second rotation axis which extends parallel to the first rotation axis.

On the end of the lever 30, on the opposite side from the second rotation unit 28, a receiving unit 32 is provided, on which the laparoscope 100 is secured. This receiving unit 32 is designed in such a manner that the laparoscope 100 is secured in a rotatable manner on the lever 30, so that only a point guidance occurs. For example, by means of the receiving unit 32, a degree of rotational freedom is made available, which would not exist in the case of a forcible guidance.

An additional pivot point is provided via the trocar point 102, wherein the orientation of the laparoscope 100 is thus always determined via the trocar point 102 and the position of the suspension point of the receiving unit 32. Thus a purely point guidance of the laparoscope 100 is achieved.

In the main body 12, a first drive unit 34 is provided, which drives the first and the second rotation unit 26, 28. For this purpose, the first drive unit 34 is formed in each case in such a manner that it rotates the first and the second rotation unit 28 by the same rotation angle, but in opposite directions. Thus, the main body 12 is rotated relative to the securing unit 14 and the lever 30 is rotated relative to the main body 12 always by the same angle but in opposite directions. The effect of this is that, if no PAN movement is carried out, the suspension point of the laparoscope 100 on the lever 30 is moved on a circular path, as a result of which the TILT movement is performed. In order to activate the PAN movement, the suspension point can thus be moved overall, not only on a circular path, but also on a spherical surface about the trocar point 102.

Thus, the TILT movement occurs exclusively by means of the first drive unit 34 and the corresponding synchronous opposite driving of the rotation unit 26, 28. The ZOOM movement is achieved exclusively by the change in the distance between the two housing parts 20, 22 produced by means of the second drive unit 24. The PAN movement, on the other hand, is achieved exclusively by the rotation of the main body 12 about the third rotation axis 18 with the aid of the securing unit 14.

Thus, overall, a direct driving is achieved, in which each of the three basic movements can be carried out very simply via its own drive unit 24, 34, 90. For example, no expensive controls are needed, and no curve interpolations have to be carried out. Thus, the control can occur via an image processing program, without the need for sensors for the detection of the current position and orientation.

Figure 3:
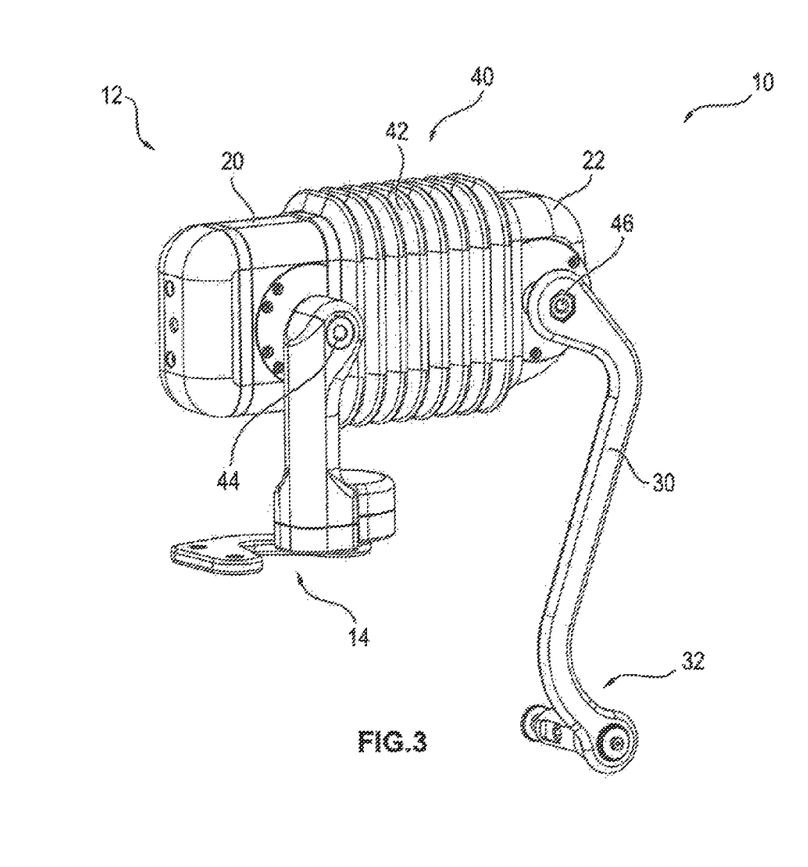
FIG. 3 shows a diagrammatic perspective representation of a device for retaining and moving a laparoscope according to a first embodiment.

In FIG. 3, a diagrammatic perspective representation of a device 10 for retaining and moving a laparoscope 100 during an operation according to a first embodiment is represented. The main body 12 has a housing 40 which comprises a first housing part 20, a second housing part 22 as well as a foldable bellows 42 arranged between the first and the second housing part.

From the first housing part 20, a first shaft 44 of the first rotation unit 26 protrudes, on which the securing unit 14 is mounted in a rotationally fixed manner.

In the same way, from the second housing part 22, a second shaft 46 of the second rotation unit 28 protrudes, on which again the lever 30 is mounted in a rotationally fixed manner. The receiving unit 32 for securing the laparoscope 100 is here shown only diagrammatically. The laparoscope 100 itself is not shown.

Figure 4:
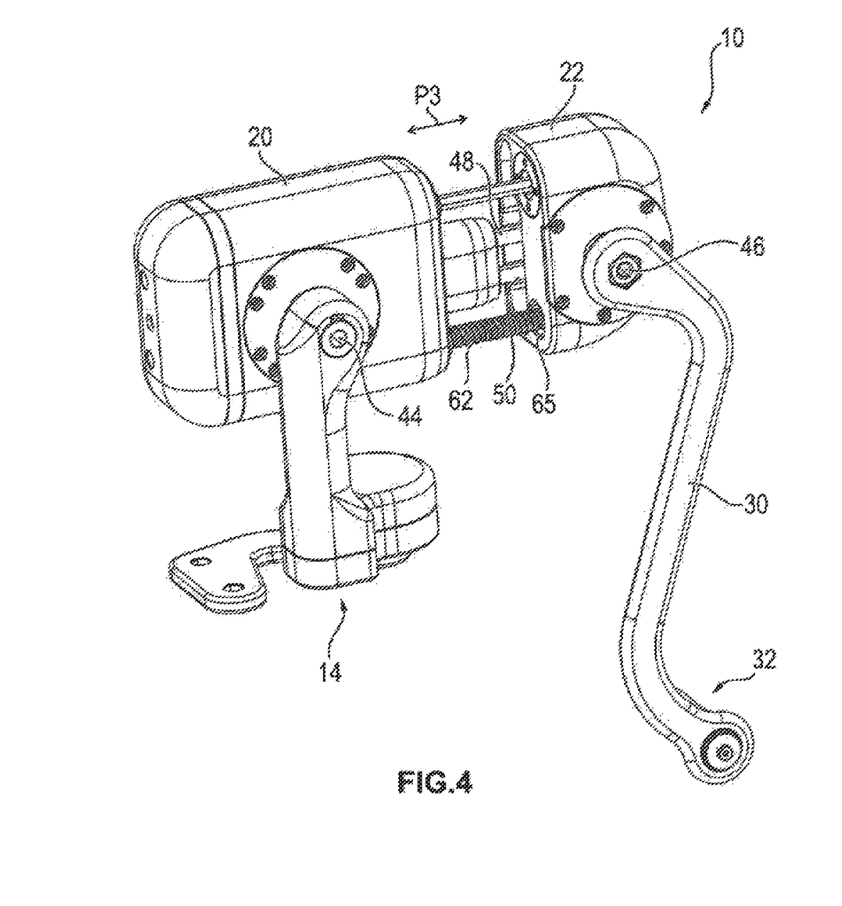
FIG. 4 shows an additional diagrammatic perspective representation of the device according to FIG. 3 with the bellows not shown.

In FIG. 4, an additional diagrammatic perspective representation of the device 10 according to FIG. 3 is shown, wherein the bellows 42 is not shown. As one can now see, the two housing parts 20, 22 are completely separate from one another, and they can be moved toward one another or apart from one another in accordance with the double arrow P3. Depending on the distance between the two housing parts 20, 22, the distance between the two shafts 44, 46 changes, and thus the distance between the lever 30 and the securing unit 14 changes. This in turn has the result that, due to the change in the distance between the two housing parts 20, 22 with respect to one another, the laparoscope 100 is moved translationally in the direction of its longitudinal axis, so that a ZOOM movement is performed.

The two housing parts 20, 22 are connected to one another via two linear guides 48, 50 which enable the linear shifting of the two housing parts 20, 22 with respect to one another and nevertheless ensure force transmission, so that the forces acting on the laparoscope 100 can be transferred to the retaining arm and canting can be prevented.

Figure 5:
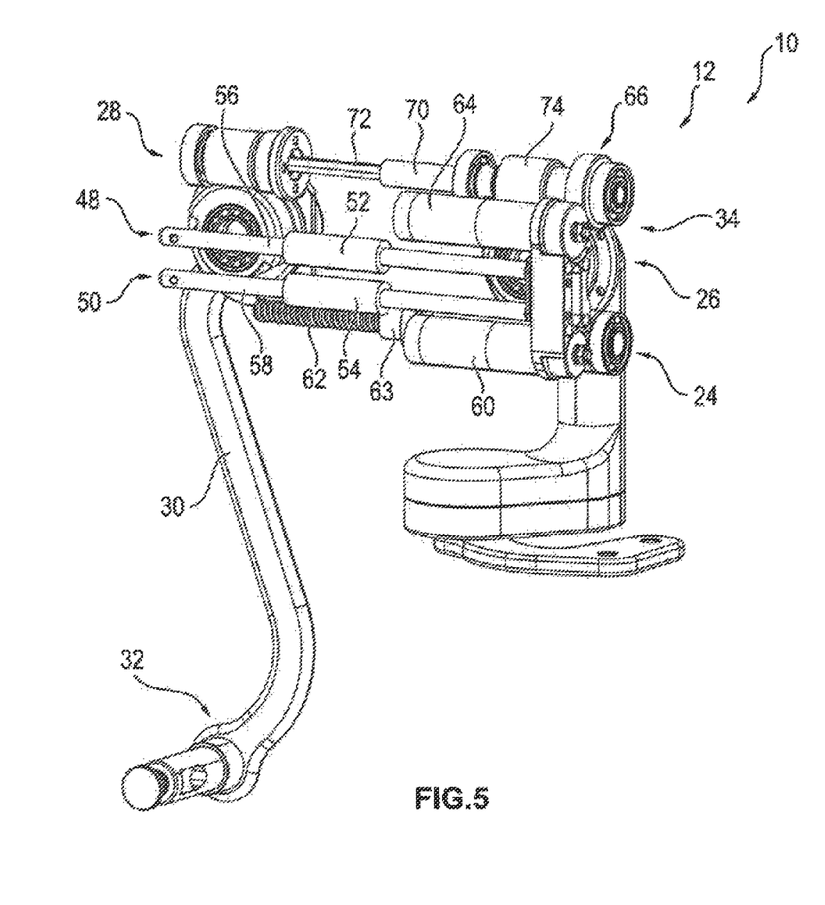
FIG. 5 shows a diagrammatic perspective representation of the device according to FIGS. 3 and 4 with the housing not shown.

In FIG. 5, an additional diagrammatic perspective representation of the device according to FIGS. 3 and 4 is shown, wherein the housing 40 is completely hidden here, in order to reveal components located within the housing 40, for example the first and the second drive unit 34, 24. Here, in FIG. 5, the view is directed toward opposite side compared to FIGS. 3 and 4.

The linear guides 48, 50 each consist of a ball bushing 52, 54 in which round guides 56, 58 are guided.

The second drive unit 24 comprises a motor 60, via which a spindle nut 63 can be driven. A spindle 62 is mounted on the side of the first housing part 20 in the spindle nut 63. The opposite end of the spindle 62 is mounted in a recess 65 of the second housing part 22. By rotating the spindle nut 63, depending on the rotation direction of the spindle 62, the second housing part 22 is moved toward the first housing part 20 or away from the first housing part 20.

The first drive unit 34 for driving the rotation units 26, 28 comprises a motor 64 which drives an upright shaft 68 via a gear wheel arrangement 66. The upright shaft 68 is here designed so it can be telescoped, i.e., it comprises two shafts 70, 72 which can be shifted linearly relative to one another and which are rotationally fixed. Thus, via a motor 64, a driving of the rotation units 26, 28 arranged in the different housing parts 20, 22 can occur, and, nevertheless, an adjustment of the distance between the housing parts 20, 22 can be ensured.

Figure 6:
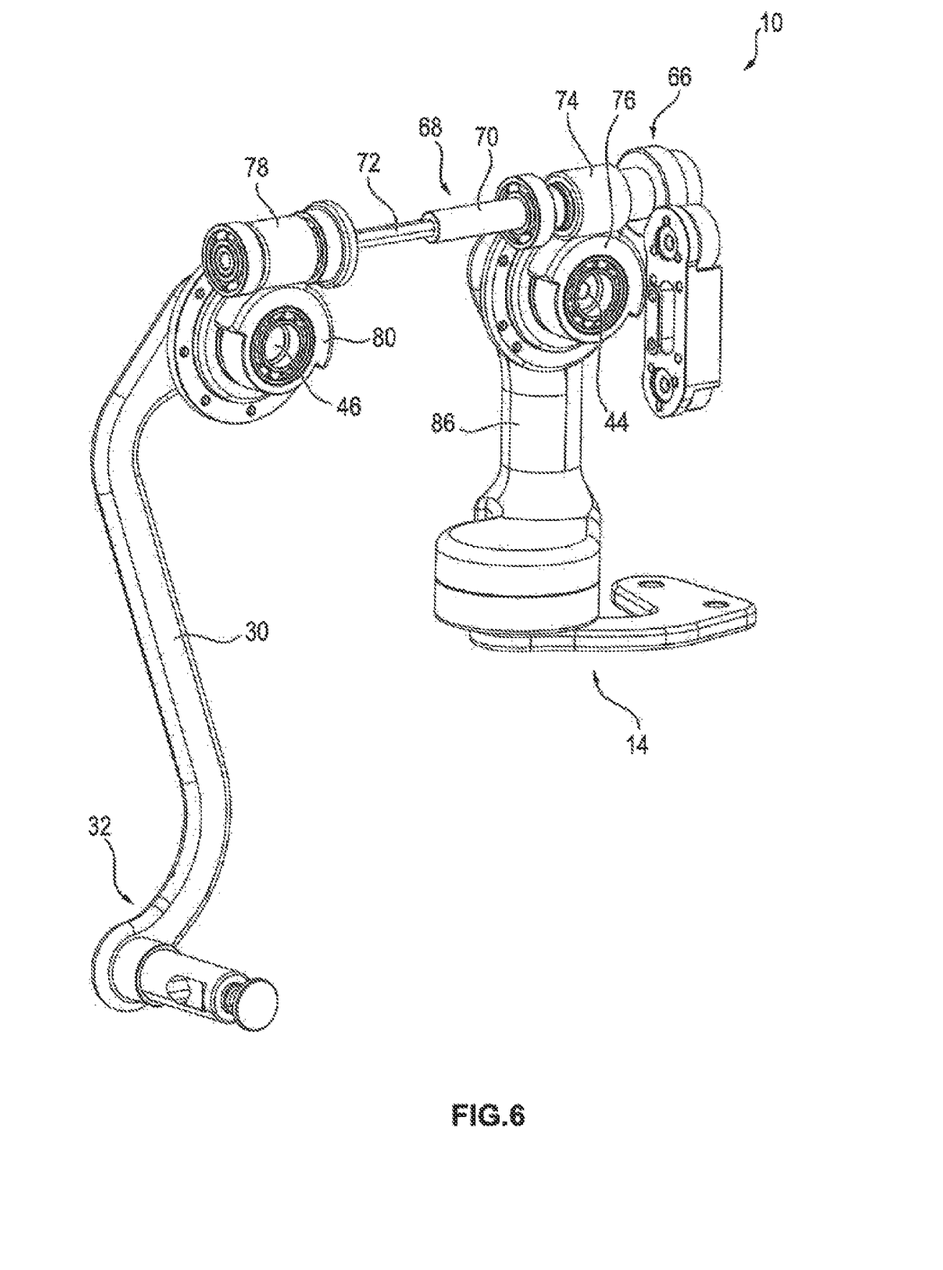
FIG. 6 shows a diagrammatic perspective representation of a section of the device according to FIGS. 3 to 5.

On the upright shaft 68, a first worm 74 is arranged, which, as shown in FIG. 6, is in engagement with a first worm gear 76. The worm gear 76 is mounted in a rotationally fixed manner on the first shaft 44.

Furthermore, on the upright shaft 68, a second worm 78 is arranged, which is in engagement with a second worm gear 80 which in turn is mounted in a rotationally fixed manner on the second shaft 46 of the second rotation unit 28.

The worms 74, 78 and the worm gears 76, 80 are here designed in such a manner that the rotation of the shafts 44, 46 occurs during the rotation of the upright shaft 68 via the motor 64 by the same rotation angle in the opposite rotation direction. As a result, in a simple manner, the guidance of the suspension point of the laparoscope 100 on a circular path, which is described in connection with FIG. 2 and required for the TILT movement, is achieved.

In FIG. 7, a diagrammatic perspective representation of the securing unit 14 is shown. The securing unit 14 has a first section 82 as well as a second section 84, wherein the second section 84 is designed in such a manner that it can be secured via a quick release connector, which is not shown, on a retaining arm 16. The two sections 82, 84 are connected to one another in such a manner that they can be rotated relative to one another about the third rotation axis 18. For this purpose, within the housing 86 of the first section 82, a third drive unit 90 is provided, which is shown in FIG. 8. The third drive unit 90 comprises a motor 92, with the aid of which a shaft 94 can be rotated, which is connected in a rotationally fixed manner to the second section 84. For this purpose, the motor 90 is connected to the shaft 94 via a gear wheel arrangement 96. For example, the third drive unit 90 is mounted here completely on a rolling bearing. The connection to the driveshaft of the motor 92 is established, for example, via a spur gear cascade.

In FIG. 9, a diagrammatic representation of a main body 202 of a device 200 according to a second embodiment is represented. Elements that have the same structure or the same function have the same reference numerals as in the first embodiment. In contrast to the embodiment according to FIGS. 3 to 8, the motors 60, 64 of the first and the second rotation unit 34, 24 are here arranged rotated by 180°.

However, the embodiment according to FIGS. 3 to 8 has the advantage that its design is more compact.

Figure 10:
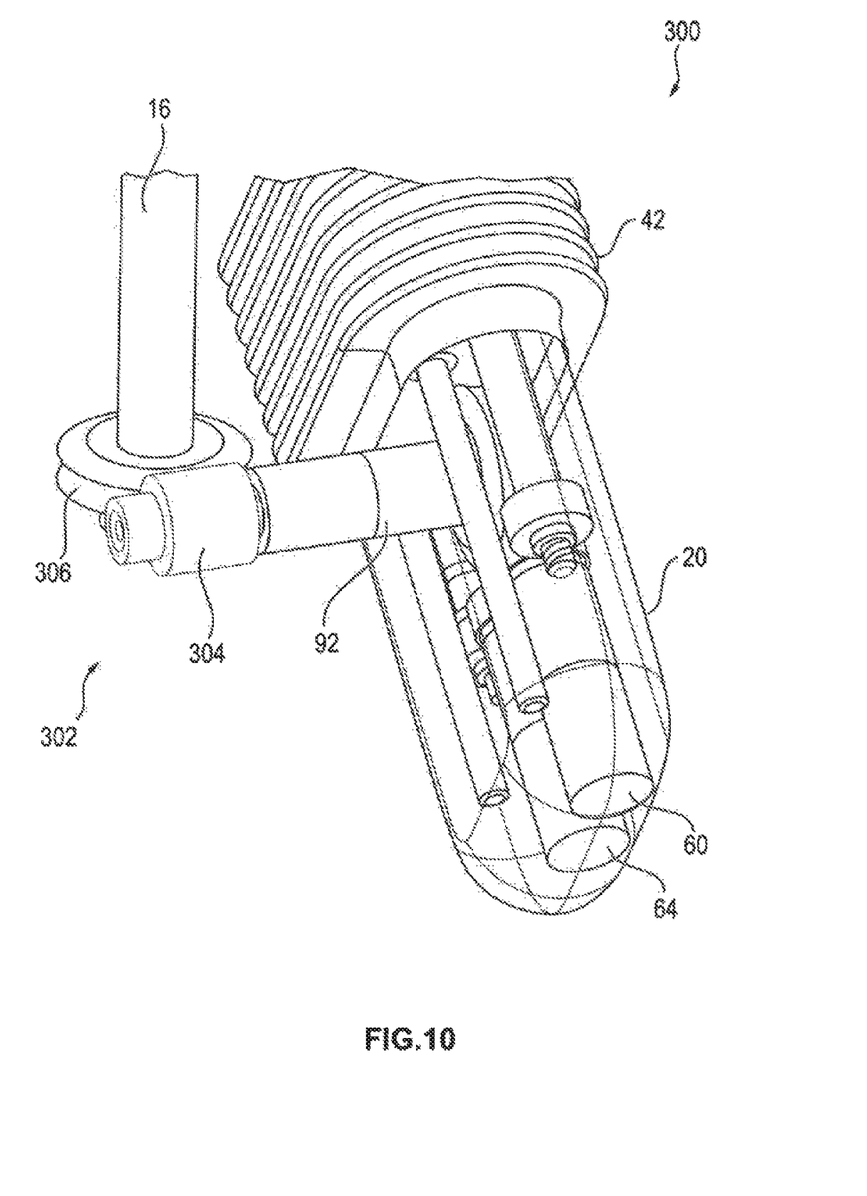
FIG. 10 shows a diagrammatic perspective representation of a securing unit of a device for retaining and moving a laparoscope according to a third embodiment.

In FIG. 10, a diagrammatic representation of a section of a device 300 according to a third embodiment is shown, wherein here, for example, the securing unit 302 has a different design. The securing unit comprises a worm 304 which is driven via the motor 92 and which is in engagement with the worm gear 306.

In addition, here, in contrast to the first embodiment, the motor 92 is also arranged at least partially within the housing 40 of the main body 12.

For example, on the securing unit 14, 302 a laser can be provided in each case, with the aid of which the orientation onto the trocar point 102 can occur. Alternatively, the orientation can also occur, for example, via a separate setting gauge.

The lever 30 is designed for example in such a manner that it contains no inner components and thus has a very simple design. Thus, the lever can be implemented as a disposable article or as an article made of a sterilizable material.

For example, the lever 30 has an S-shaped design, as a result of which the surgeon is provided with the most room possible in order to be able to rotate the laparoscope 100, if necessary, as well as to the best possible extent about its longitudinal axis.

All the above-described devices 10, 200, 300 have the advantage that each of the movements, that is to say the PAN movement, the TILT movement and the ZOOM movement, is driven by its own drive unit 24, 34, 90. Thus, the device 10, 200, 300 makes do without a sensor system, which leads to an increased reliability. In addition, the control is relatively simple, since, in each case, only one drive unit 24, 34, 90 needs to be activated for the basic movements. In addition, the manufacturing costs incurred are low.

Furthermore, the devices 10, 200, 300 have the advantage that they have a compact and relatively light-weight structure. Thus, they can be mounted without problem on the slide rails of the operating table, so that adjustment of the operating table is possible without the need for a post-readjustment of the devices 10, 200, 300.

In addition, the devices 10, 200, 300 are independent of the retaining arm, i.e., in that all the components required for the movement of the laparoscope 100 are arranged in the device 10 itself. Thus, the individual components can be handled easily, since they can be installed one after the other on the operating table. Thus, the system can be mounted by a single person and its pack size is small.

In addition, the effort for the initial orientation on the trocar point 102 is very low. In contrast to many known systems, no expensive sensor system that must be initialized by reference runs is necessary.

Due to the point guidance and the articulated suspension of the laparoscope 100 on the lever 30, errors up to a few centimeters in the orientation onto the trocar point 102 can be tolerated without the occurrence of injuries to the patient and/or damage to the devices 10, 200, 300 and/or the laparoscope 100.

In addition, the devices 10, 200, 300 have only a very small interfering contour. Around the trocar point 102, much freedom of movement exists for the introduction of the work trocar and the movement of the laparoscopic instruments. This is achieved for example by the use of a very slender suspension arm for the fixation of the optical system. Moreover, this arm can be implemented in the form of sterile disposable components or in the form of a sterile part, so that no interfering sterile covering in the work area directly over the operating area is required.

In addition, the devices 10, 200, 300 do not require any external cable in the sterile area.

The central orientation of the devices 10, 200, 300 over the patient 106 leads to the fact that the surgeon experiences only minimal restriction of his/her freedom of movement. Since the area immediately over the abdominal wall of the patient 106 is free of mechanical elements, the trocar sleeve can be pulled back without restriction or collisions.

The articulated suspension of the laparoscope 100 on the lever 30 leads to a point guidance, which in turn minimizes the risk of mechanical tensioning and thus minimizes the occurrence of forces which can act on the abdominal wall of the patient 106 or the clamped in laparoscope 100. As a result, the patient safety is increased, and the risk of damage to the laparoscope 100 is reduced.

In addition, the devices 10, 200, 300 have a compact structure, and pinching and shearing sites are minimized since the housing 40 is enclosed on all sides, and a good cleanability is made possible.

The swan-necked design of the lever 30, via which the laparoscope 100 is secured, allows a very large angular range for the rotation of the laparoscope 100.

In addition, the devices 10, 200, 300 are self-locking due to the use of worm gears 74, 76, 78, 80, so that braking can be dispensed with. Furthermore, the safety in the case of an interruption of the power supply is increased, since the worm gears automatically prevent a movement in the currentless state.

It will be apparent to those skilled in the art that various modifications and variations can be made to the present disclosure without departing from the scope of the disclosure. Other embodiments of the disclosure will be apparent to those skilled in the art from consideration of the specification and practice of the teachings disclosed herein. It is intended that the specification and embodiments described herein be considered as exemplary only.

We claim:

1. A device for retaining and moving a laparoscope during an operation, comprising:
    a securing unit for securing the device on a retaining arm,
    a receiving unit for retaining the laparoscope,
    a main body, and
    a lever via which the receiving unit is secured to the main body,
    wherein the main body is mounted on the securing unit in a rotatable manner about a first rotation axis via a first rotation unit,
    wherein the lever is mounted on the main body in a rotatable manner about a second rotation axis via a second rotation unit,
    wherein a first drive unit, upon activation, drives the first and the second rotation unit, in such a manner that the main body is rotated about the first rotation axis and the lever is rotated about the second rotation axis by the same rotation angle in opposite rotation directions,
    wherein the main body comprises a housing which comprises a first housing part and a second housing part which is separate from this first housing part, and that the first rotation unit is mounted on the first housing part and the second rotation unit is mounted on the second housing part, and
    wherein a second drive unit linearly moves the second housing part relative to the first housing part along a predetermined distance.

2. The device according to claim 1, wherein the first rotation unit comprises a first shaft on which the securing unit is mounted in a rotationally fixed manner, that the second rotation unit comprises a second shaft on which the lever is mounted in a rotationally fixed manner, and that the first and the second shaft are rotated via the first drive unit in opposite rotation directions by the same rotation angle.

3. The device according to claim 1, wherein the first drive unit comprises exactly one motor via which the first and the second rotation unit are driven.

4. The device according to claim 3, wherein the first drive unit comprises an upright shaft, which is driven via the motor, and that the upright shaft drives the two rotation units.

5. The device according to claim 4, wherein the upright shaft is in engagement via a first worm gear wheel arrangement or bevel gear wheel arrangement with the first shaft of the first rotation unit, and that the upright shaft is in engagement via a second worm gear wheel rotation unit arrangement or bevel gear wheel arrangement with the second shaft.

6. The device according to claim 3, wherein the motor drives the rotation units via chain and/or belt drives and/or hydraulic couplings.

7. The device according to claim 1, wherein the first drive unit comprises two motors, wherein in each case one motor is used for driving one rotation unit, and that a control unit is provided, which synchronously activates the two motors.

8. The device according to claim 1, wherein the receiving unit is designed in such a manner that via it the laparoscope can freely rotate on the lever.

9. The device according to claim 1, wherein the second drive unit comprises a motor and a spindle nut driven by said motor, and that the first and the second housing part are coupled to one another via a spindle guided in the spindle nut.

10. The device according to claim 1, wherein the first and the second housing part are connected to one another via at least one linear guide.

11. The device according to claim 1, wherein the housing comprises a foldable bellows and/or a telescopic sheet metal covering, which is/are arranged between the first and the second housing part.

12. The device according to claim 1, wherein the first housing part can be shifted at least partially onto the second housing part or the second housing part can be shifted at least partially onto the first housing part.

13. The device according to claim 1, wherein the first drive unit, the second drive unit, the first rotation unit and/or the second rotation unit are each arranged at least partially or completely within the housing.

14. The device according to claim 1, wherein the securing unit comprises a first section and a second section, and that the first section can be rotated about a third rotation axis relative to the second section.

15. The device according to claim 14, wherein a third drive unit for the rotation of the first section relative to the second section is provided.

16. The device according to claim 15, wherein the third drive unit is arranged at least partially in a housing of the main body.

17. The device according to claim 15, wherein the third drive unit is arranged at least partially in a housing of the securing unit.

18. The device according to claim 14, wherein the third rotation axis is arranged orthogonally with respect to the first and second rotation axes.

19. The device according to claim 15, wherein the device comprises a retaining arm for securing the device on an operating table, and that the third drive unit is arranged within this retaining arm.

20. A device for retaining and moving a laparoscope during an operation, comprising:
- a securing unit for securing the device on a retaining arm,
- a receiving unit for retaining the laparoscope,
- a main body comprising a housing having a first housing part and a second housing part which is separate from the first housing part, and
- a lever via which the receiving unit is secured to the main body, wherein the main body is mounted on the securing unit in a rotatable manner about a first rotation axis via a first rotation unit, wherein the lever is mounted on the main body in a rotatable manner about a second rotation axis via a second rotation unit, wherein a first drive unit is provided, which, upon activation, drives the first and the second rotation unit, in such a manner that the main body is rotated about the first rotation axis and the lever is rotated about the second rotation axis by the same rotation angle in opposite rotation directions, wherein the main body comprises a housing which comprises a first housing part and a second housing part which is separate from this first housing part, and that the first rotation unit is mounted on the first housing part and the second rotation unit is mounted on the second housing part, and wherein the first housing part and the second housing part are connected to one another via a first linear guide and a second linear guide, thereby enabling the linear shifting of the first housing part and the second housing part.

* * * * *